United States Patent [19]

Nelson et al.

[11] Patent Number: 4,484,014

[45] Date of Patent: Nov. 20, 1984

[54] HYDROCARBON SYNTHESIS

[75] Inventors: William T. Nelson; Ernest A. Zuech, both of Bartlesville, Okla.

[73] Assignee: Phillips Petroleum Company, Bartlesville, Okla.

[21] Appl. No.: 490,755

[22] Filed: May 2, 1983

[51] Int. Cl.³ .......................... C07C 3/21; C07C 3/62
[52] U.S. Cl. .................................. 585/255; 585/316; 585/328; 585/329; 585/517; 585/524
[58] Field of Search ............... 585/255, 315, 316, 328, 585/329, 517, 525, 310, 324

[56] References Cited

U.S. PATENT DOCUMENTS

| | | | |
|---|---|---|---|
| 3,391,219 | 4/1962 | Davis et al. | 585/517 |
| 4,300,006 | 11/1981 | Nelson | 585/255 |
| 4,319,064 | 3/1982 | Heckelsberg et al. | 585/255 |
| 4,420,646 | 12/1983 | Darden et al. | 585/255 |

OTHER PUBLICATIONS

O'Connor et al., Analytical Chemistry, 32(6), 701–706, (1960).
Sista et al., Analytical Chemistry, 48(11), 1582–1583, (1976).
Bowen, Analytical Chemistry, 48(11), 1984, (1976).

Primary Examiner—Delbert E. Gantz
Assistant Examiner—A. Pal
Attorney, Agent, or Firm—Bernhard H. Geissler

[57] ABSTRACT

A lube-oil range hydrocarbon mixture is produced by the oligomerization of a branched olefin mixture which contains olefins of 6 to 16 carbon atoms and has a degree of branching of about 10 to 50 mole percent of branched olefins; the lube-oil range hydrocarbon is obtained by separating and hydrogenating the oligomerized olefins.

6 Claims, No Drawings

ABSTRACT OMITTED - beginning content

HYDROCARBON SYNTHESIS

This invention relates to the catalytic conversion of olefins into higher hydrocarbons. More specifically this invention relates to the production of saturated hydrocarbons. In a yet further aspect of this invention a process for producing lube-oil range hydrocarbons from ethylene is provided.

BACKGROUND OF THE INVENTION

The art of converting olefins into higher hydrocarbons is a mature technology. Catalytic dimerization, oligomerization and polymerization processes have been developed. It is known in the art, for instance, that normal alpha olefins can be oligomerized into lube-oil range hydrocarbons using boron trifluoride catalysts together with alcohol promoters. Such a process is described in U.S. Pat. No. 3,780,128. It is also known that the normal alpha olefins used for this process can be obtained by ethylene chain growth using ethylene as a starting material and a catalyst such as triethylaluminum.

Production of lube-oil range hydrocarbons from pure monomers such as 1-decene is generally prohibitive from a commercial standpoint in view of the high cost of producing the pure normal alpha olefin. For similar reasons mixtures of normal alpha olefins are not particularly desirable feedstocks for the production of lube-oil range hydrocarbons. It is therefore a continuing goal to provide processes for the production of such hydrocarbons which utilize other feedstocks.

THE INVENTION

It is thus one object of this invention to provide a process for the production of higher hydrocarbons from olefins.

Another object of this invention is to provide a process for the conversion of ethylene to lube-oil range hydrocarbons.

A yet further object of this invention is to provide a feedstock for an oligomerization process in which an olefin feedstock is used to produce lube-oil range hydrocarbons.

These and other objects, advantages, details, features and embodiments of this invention will become apparent to those skilled in the art from the following detailed description of the invention and the appended claims.

In accordance with this invention, a process for the production of hydrocarbons is provided which comprises the catalytic conversion of an olefin feedstock which comprises a mixture of olefins having 6 to 16 carbons atoms and containing about 5 to 60, preferably 10 to 50 mole percent branching in the presence of boron trifluoride as a catalyst. The most preferred mixture of olefins used is one that has 8 to 16 carbon atoms. The lube-oil range hydrocarbon mixture is separated from the oligomerization product and after hydrogenation a hydrocarbon oil is obtained as the product of the process.

In accordance with a preferred embodiment of this invention ethylene is contacted with a trialkylaluminum catalyst to produce an olefin mixture containing about 5 to 60, more specifically 10 to 50 and preferably 20 to 35 mole percent branching in the $C_6$–$C_{16}$ range and the $C_6$–$C_{16}$ range olefin mixture is separated from the ethylene growth product. Thereafter this olefin mixture in the $C_6$–$C_{16}$ range is oligomerized in the presence of a boron trifluoride catalyst and a lube-oil range hydrocarbon mixture is separated from the so obtained oligomerization product. This lube-oil range hydrocarbon finally is hydrogenated to yield a saturated hydrocarbon oil as the product of the process.

The oil produced after hydrogenation preferably has a VI of at least 110 and a pour point of at least $-35°$ C. or lower.

ETHYLENE CHAIN GROWTH

The ethylene chain growth, when employed in accordance with the preferred embodiment of this invention, is carried out utilizing standard ethylene chain growth catalysts. The preferred catalyst for this step is trialkylaluminum. The alkyl radicals of these trialkylaluminum catalyst have 1 to 8 carbon atoms. The triethylaluminum catalyst is presently particularly preferred.

The ethylene chain growth reaction is carried out under conditions that the olefin mixture in the $C_6$–$C_{16}$ range has a degree of branching in the range of about preferably 10 to about 50 mole percent. The mole percent branching is determined by hydrogenating the olefin mixture, e.g. the ethylene growth product and measuring the mole percent of branching of the so hydrogenated product by gas phase chromatography. When a trialkylaluminum catalyst is used, these chain growth conditions are:
temperature in the range of 180°–250° C.
total pressure 1,000 to 50,000 psig, preferably 2,000 to 5,000 psig.

It should be noted that generally speaking, the ethylene chain growth in order to produce the feedstock useful in accordance with this invention will be carried out at a temperature significantly above that temperature which would produce normal alpha olefins. The temperature will generally be at least about 20° C. above the temperature range in which the ethylene chain growth yields essentially only normal alpha olefins.

The ethylene chain growth process step can be carried out using ethylene as such. Or it can be carried out in the presence of a diluent. Examples for such a diluent are normal paraffins such as those with 5 to 7 carbon atoms per molecule. The ethylene chain growth step is preferably carried out in the liquid phase. The process conditions for this step therefore are high pressure and medium temperature conditions. Preferably the pressure is in the range of 2,000 to 5,000 and the temperature is in the range of 180° to 250° C.

SEPARATION OF OLEFIN MIXTURE

A second, optional but preferred step in the overall process of this invention comprises separating the branched olefins having about 6 to about 16 carbon atoms from the product obtained in the ethylene chain growth step. This separation can be done in a variety of ways known to persons skilled in the art. The presently preferred operation is a distillation separation. The distillation or other separation is carried out to yield a product comprising olefins having about 6 to about 16 carbon atoms and having about 5 to 60 mole percent branching, this mole percentage being based on the total quantity of olefins in the product.

The usually employed conditions for separating the olefin mixture from the oligomerization product of the ethylene chain growth are vacuum distilled in a Vigreux column (after first trapping $C_4$ and lighter olefins) to a cut point of about 150° C. at 1 torr pressure to recover $C_6$ through $C_{16}$ olefins.

OLIGOMERIZATION WITH BF$_3$

In order to obtain a lube-oil range hydrocarbon the olefin mixture characterized above and having the degree of branching described is subjected in accordance with this invention to an oligomerization step utilizing a BF$_3$ catalyst. The catalyst is preferably used together with a promoter, particularly an alcohol promoter and most preferably with an alcohol having 2 to 3 carbon atoms. The promoter is used in a quantity of 50 to 200 mole percent based on BF$_3$. The total catalyst is used preferably in the process of this invention in a concentration of 3 to 5 wt. % based on total olefins.

The oligomerization conditions for this step in the process of this invention are specified in the following table:

| Oligomerization Conditions Using BF$_3$ Catalyst | | |
|---|---|---|
| | Generally Employed | Preferred |
| Temperature, °C. | 40 | 40–80 |
| Pressure, psig | 25 | 0–50 |
| Contact Time | 15 | 5–30 |

SEPARATION

From the BF$_3$ oligomerization mixture a lube-oil range hydrocarbon mixture is recovered. The separation is most preferably done by distillation or fractionation. The lube-oil range hydrocarbon recovered is generally characterized by a boiling point in the range of 390° to 550° C., preferably in the boiling point range of 400° to 510° C.

The separation of the lube-oil range hydrocarbon mixture can be carried out prior to or following the hydrogenation step. If the separation is carried out prior to hydrogenation, the distillation is preferably effected under vacuum, e.g. at a pressure of 0.5 to 1 torr. If the separation is carried out with the hydrogenated material, the distillation of fractionation may be carried out under normal pressure conditions.

HYDROGENATION

The olefins material obtained by the oligomerization with BF$_3$ is subjected, in accordance with this invention, to a hydrogenation step. Typical hydrogenation catalysts which are useful for this step are palladium on charcoal and nickel on alumina. Typical hydrogenation conditions for the hydrogenation step are

| Hydrogen partial pressure | 100 to 1,000 psig |
|---|---|
| Temperature | 100 to 200° C. |
| Contact time in an autoclave | 0.1 to 2 hours |

RECYCLE

It is presently preferred, although not required in accordance with this invention, that the unreacted ethylene in the ethylene chain growth reaction be recycled. Similarly it is preferred that the olefins remain unreacted after the oligomerization step or the olefins remaining after the fraction of C$_6$–C$_{16}$ olefins has been separated from the oligomerization mixture be recycled to the oligomerization step.

The following examples further illustrate preferred features and embodiments of this invention but are not intended to unduly limit the scope thereof.

ETHYLENE GROWTH STEP

The ethylene growth runs were made in a 875 mL stirred autoclave. The entire interior surface was copper-plated to minimize undesirable side reactions.

The evacuated reactor was charged with 700 psig ethylene, heated to 15° C. below the intended reaction temperature, then pressured with more ethylene to 3200 psig. At this point triethylaluminum (TEA) dissolved in n-hexane was added to the reactor. Initation of the reaction was apparent in the rapid increase in temperature and sharp decrease in pressure. Cooling coils were used to control the temperature and a compressor to maintain the 3200–3400 psig pressure. After 30–80 minutes the reactor temperature was reduced to 10° C., the compressor was stopped, and the reaction was quenched with a 10-fold excess of methanol, destroying any aluminum alkyl compounds present.

A transfer vessel containing the product was cooled to dry-ice (CO$_2$) temperature. The product was then washed with 10% NaOH (aqueous). The organic layer was then dried with mole sieves.

The product is a mixture of C$_4$–C$_{20}$ olefins (1% > C$_{20}$). Gas chromatographic analysis of a hydrogenated sample showed the distribution of olefins and the percent branched molecules. The product was distilled. The C$_6$–C$_{16}$, or respectively C$_8$–C$_{16}$ fraction was used as a feedstock for the oligomerization step.

BF$_3$/N-PROPANOL CATALYZED OLIGOMERIZATION OF OLEFIN FRACTION

The oligomerization runs were made in a 300 mL Hastelloy B autoclave.

About 100 g of olefin and 2 g n-propanol were charged to this reactor. After cooling to 10° C. and evacuation, 3 g BF$_3$ gas were charged into the reactor at 50 psig. Temperature was maintained at 40°–50° C. for 10–15 min. reaction time.

After cooling to 25° C. the product was transferred to a flask and diluted with 100 mL hexane. A catalyst phase separated, comprising all the propanol and about ½ the BF$_3$. The remainder of the BF$_3$ was in the gas phase. The product phase was washed with aqueous ammonium hydroxide and dried over mole sieve.

DISTILALTION AND HYDROGENATION

The dried product was stripped of n-hexane in a rotary evaporator and vacuum distilled on a 10-inch Vigreux column. The lube-oil fraction was recovered distilling between 400° and 485° to 540° C. This fraction was then hydrogenated using 0.25 g of 10% Pd/C catalyst for 2 hrs at 160° C. and 400 psig H$_2$ pressure.

Experimental quantities and conditions for typical runs are given in the table I along with an oligomerization run with 1-decene for comparative purposes. Note: in the ethylene growth run #5 done at the highest temperature, the product was so highly branched, (about 55% in C$_8$–C$_{16}$ fraction) that an oligomerization reaction time of 1 hr gave only 91% conversion, and of that, one third to dimers too light for synthetic lube-oils.

TABLE I

| Ethylene Growth Runs | 1 | 2 | 3 | 4 | 5 |
|---|---|---|---|---|---|

TABLE I-continued

| | | | | | |
|---|---|---|---|---|---|
| Ethylene/TEA (mole ratio) | 1200 | 1560 | 1505 | 1465 | 1735 |
| Ave. reaction temp. °C. | 217 | 220 | 234 | 235 | 244 |
| Ave. pressure, psig | 3260 | 3435 | 3410 | 3410 | 3190 |
| Contact Time, min. | 45 | 80 | 45 | 80 | 80 |
| Ethylene Conversion, wt % | 62 | 90.3 | 79.5 | 88.4 | 86.8 |
| Yield, wt % | | | | | |
| $C_4$ | 14.0 | 24.8 | 22.6 | 21.8 | 23.7 |
| $C_6$ | 11.3 | 18.2 | 19.0 | 20.6 | 23.0 |
| $C_8$ | 11.5 | 13.8 | 14.4 | 16.1 | 17.0 |
| $C_{10}$ | 7.7 | 10.3 | 9.2 | 11.1 | 10.5 |
| $C_{12}$ | 5.4 | 7.4 | 5.6 | 7.2 | 5.9 |
| $C_{14}$ | 3.8 | 5.0 | 3.3 | 4.4 | 3.1 |
| $C_{16}$ | 2.9 | 3.3 | 1.9 | 2.6 | 1.5 |
| $C_{18}+$ | 5.4 | 7.5 | 3.5 | 4.6 | 2.1 |
| Branching in $C_8$-$C_{16}$, % | 10 | 21 | 32 | 46.5 | 54.5 |

| | $BF_3$/n-propanol Catalyzed Oligomerization Runs | | | | | |
|---|---|---|---|---|---|---|
| Oligomerization Run[1] | 1 ($C_8$-$C_{16}$) | 2 ($C_6$-$C_{16}$) | 3 ($C_8$-$C_{16}$) | 4 $C_8$-$C_{16}$ | 5 ($C_8$-$C_{16}$) | 6 ($C_{10}$) |
| Olefin Conversion, wt % | 95 | 96 | 97.7 | 92.8 | 89 | 98 |
| Yield, wt % | | | | | | |
| lights (<400° C.) | 1.8 | 7.3 | 6.1 | 28.8 | 33.8 | 4 |
| Lube Oil | 59.8 | 82.5 | 84.7 | 60.0 | 49.6 | 90 |
| | 400–520° C. | 400–530° C. | 400–530° C. | 400–510° C. | 400–485° C. | 400–530° C. |
| Heavies | 34.4 | 6.2 | 6.9 | 4.0 | 5.6 | 4 |
| | >520° C. | >530° C. | >530° C. | >510° C. | >485° C. | >530° C. |
| Lube Oil Properties | | | | | | |
| Overall yield from ethylene, wt % | 19 | 48 | 29 | 25 | 19 | — |
| Viscosity index (41–46 SUS @ 100° C.) | 133 | 124 | 112 | 112 | 102 | 135 |
| Pour point, °C. | −40 | −40 | −48 | −51 | −46 | <−51 |

[1]Runs 1-5 used the $C_8$-$C_{16}$ or $C_6$-$C_{16}$ fraction from ethylene growth runs 1-5 respectively above; run 6 used 1-decene.

These data show that a good quality synthetic oil may be prepared from ethylene which is comparable to the more expensive 1-decene product.

The data of the following table further substantiates this.

TABLE II

Oxidation Stability of a Hydrogenated Lube-Oil Sample
Rotary Bomb Oxidation Test @ 150° C.-Copper Catalyst
(All Samples Contained 1.0 wt. % L-1395[a])

| Sample | Minutes to 25 psi ΔP |
|---|---|
| Olig. Run 3, Table I | 135 |
| SAE 10 Stock mineral oil | 100 |
| SAE 20 Stock mineral oil | 78 |
| Gulf 4cS Synfluid[b,c] | 148 |
| Olig. Run 6[b], Table I | 145 |

[a]Commercial zinc dialkyldithiophate - lubricant antioxidant
[b]Poly(1-decene)
[c]Mfg by Gulf Oil Corp.

The data in Table II show the mineral oil samples oxidize more rapidly (78–100 minutes to react with 25 psi $O_2$) than do the synthetic lubricants (135–148 minutes to react with 25 psi $O_2$). The L-1395 manufactured by Lubrizol Corp. is generally added to motor oil lubricants as an antioxidant, antiwear component.

Reasonable variations and modifications which will becomes apparent to those skilled in the art can be made from this invention without departing from the spirit and scope thereof.

What is claimed is:

1. Process for producing hydrocarbons comprising:
   (a) contacting ethylene and trialkyl aluminum as a catalyst under conditions conducive to producing an olefin mixture containing about 5 to 60 mole percent of branched olefin in the range of 6 to 16 carbon atoms such as produce an ethylene growth product, which conditions include a temperature at least 20° C. above the temperature in which this step yields essentially only normal alpha olefins,
   (b) separating an olefin mixture having about 6 to 16 carbon atoms per olefin molecule and about 5 to 60 mole percent branched olefins from the ethylene growth product,
   (c) oligomerizing said olefin mixture in the presence of a $BF_3$ catalyst to produce an oligomerization product,
   (d) separating a lube-oil range hydrocarbon mixture from said oligomerization product,
   (e) prior to or after step (d), hydrogenating at least a portion of said oligomerized hydrocarbon mixture.

2. Process in accordance with claim 1 wherein said olefin mixture contains 20 to 35 mole percent branched olefins.

3. Process in accordance with claim 1 wherein said $BF_3$ catalyst is an alcohol promoted $BF_3$ catalyst.

4. Process in accordance with claim 1 wherein said ethylene chain growth step has been carried out at a temperature in the range of about 180° to 250° C.

5. Process in accordance with claim 1 wherein said oligomerization product is separated into a lube-oil range product and a light byproduct and wherein said light byproduct is recycled to said oligomerization step.

6. Process in accordance with claim 1 wherein the hydrogenation is carried out after the separation of the lube-oil range hydrocarbon mixture from the oligomerization product.

* * * * *